United States Patent
Roessler (10) Patent No.: US 11,471,089 B2
(45) Date of Patent: Oct. 18, 2022

(54) METHOD, ECG MEASURING DEVICE, AND MEDICAL IMAGING DEVICE FOR DETERMINING AN R-WAVE IN AN ECG SIGNAL

(71) Applicant: Siemens Aktiengesellschaft, Munich (DE)

(72) Inventor: Juergen Roessler, Erlangen (DE)

(73) Assignee: Siemens Aktiengesellschaft, Munich (DE)

(*) Notice: Subject to any disclaimer, the term of this patent is extended or adjusted under 35 U.S.C. 154(b) by 1636 days.

(21) Appl. No.: 14/854,535

(22) Filed: Sep. 15, 2015

(65) Prior Publication Data

US 2016/0073919 A1  Mar. 17, 2016

(30) Foreign Application Priority Data

Sep. 16, 2014  (DE) .......................... 102014218500.9

(51) Int. Cl.
| | | |
|---|---|---|
| *A61B 5/352* | (2021.01) | |
| *A61B 5/08* | (2006.01) | |
| *A61B 5/00* | (2006.01) | |

(52) U.S. Cl.
CPC ............ *A61B 5/352* (2021.01); *A61B 5/0816* (2013.01); *A61B 5/7207* (2013.01)

(58) Field of Classification Search
None
See application file for complete search history.

(56) References Cited

U.S. PATENT DOCUMENTS

| | | | | |
|---|---|---|---|---|
| 6,493,571 B1 * | 12/2002 | Bis | ........................ | A61B 5/0555 324/307 |
| 2008/0139926 A1 * | 6/2008 | Frank | ................... | A61B 5/0456 600/413 |

(Continued)

FOREIGN PATENT DOCUMENTS

| | | |
|---|---|---|
| DE | 10200901538 A1 | 9/2010 |
| DE | 102009015385 A1 | 9/2010 |

OTHER PUBLICATIONS

M. B. I. Reaz and L. S. Wei, "Detection of the R wave peak of QRS complex using neural network," Proceedings. 2004 International Conference on Information and Communication Technologies: From Theory to Applications, 2004., Damascus, Syria, 2004, pp. 381. doi: 10.1109/ICTTA.2004.1307790 (Year: 2004).*

*Primary Examiner* — Katherine L Fernandez
*Assistant Examiner* — Michael S Kellogg
(74) *Attorney, Agent, or Firm* — Banner & Witcoff Ltd.

(57) ABSTRACT

In a method for determining R-waves in an ECG signal, at least one reference ECG signal is measured, at least one reference breathing signal is measured, at least one reference R-wave is determined using the reference ECG signal and the reference breathing signal, at least one reference value is determined using the reference ECG signal and the reference breathing signal, at least one comparison rule is credited based on the at least one reference value, ECG signals are measured and breathing signals are measured in which R-waves are to be determined, the measured ECG signals and breathing signals are compared with the at least one reference value using the at least one comparison rule, and at least one R-wave is determined using the measured ECG signals and breathing signals.

24 Claims, 3 Drawing Sheets

(56) References Cited

U.S. PATENT DOCUMENTS

| | | | |
|---|---|---|---|
| 2009/0149768 A1* | 6/2009 | Sprung | A61B 5/0205 600/523 |
| 2009/0270715 A1* | 10/2009 | Demharter | A61B 5/0402 600/411 |
| 2009/0319192 A1* | 12/2009 | Bergner | A61B 5/0428 702/19 |
| 2010/0174205 A1 | 7/2010 | Wegerif | |
| 2010/0191134 A1* | 7/2010 | Frank | A61B 5/0456 600/521 |

* cited by examiner

METHOD, ECG MEASURING DEVICE, AND MEDICAL IMAGING DEVICE FOR DETERMINING AN R-WAVE IN AN ECG SIGNAL

BACKGROUND OF THE INVENTION

Field of the Invention

The invention concerns a method for determining an R-wave in an ECG signal, as well as an ECG measuring device and a medical imaging device that implement such a method.

Description of the Prior Art

ECG measuring devices are primarily used for measuring and monitoring the cardiac function of a patient. For this purpose, the total voltage of the electrical activity of the heart muscle fibers is typically measured as what is known as an "ECG signal" by way of at least two electrodes. Characteristic curves of the ECG signal are identified according to Einthoven by the letters P, Q, R, S and T and conventionally reproduce the different phases of a heartbeat.

There are other applications besides the pure monitoring of the cardiac function of a patient. For example, ECG signals are also used in medical imaging to generate trigger signals. Information about the cardiac phase is obtained via the ECG signal during imaging in order to thereby synchronize the imaging with the cardiac activity. High quality heart scans or scans of regions which are moved by the heartbeat can be created in particular in the case of imaging methods which require a relatively long recording time.

ECG measuring devices are also used for in-situ recording of ECG signals during an examination of a patient by means of a magnetic resonance device. Operation in the magnetic resonance device places particular demands on the ECG measuring device, however, due to the strong gradient fields and high-frequency fields used therein for imaging in order to prevent mutual interference of magnetic resonance device and ECG measuring device. ECG measuring devices, which are compatible with magnetic resonance within the meaning indicated above, are commercially available.

The determination of R-waves in ECG signals is essential not just for reliable triggering. This determination is made difficult, however, for example where an ECG measuring device is used within a magnetic resonance scanner, due to T-wave superelevations that occur in the magnetic field.

Magnetic fields that change over time, as are used in a magnetic resonance scanner as magnetic gradient fields for spatial encoding, also still constitute a further, significant problem for reliable ECG signal measuring. These kinds of magnetic fields that change over time generate interference voltages in accordance with Faraday's law of induction, and these are coupled as interference into the ECG signal recorded by the ECG electrodes. Magnetically generated interference signals of this kind are superimposed on the ECG signal generated by the heart and falsify it.

These interferences are highly undesirable. Reliable detection of the R-wave of the ECG signal is necessary for synchronization of a recording of a magnetic resonance image with the heartbeat. Due to their often similar form for example, the interference signals can be erroneously interpreted as an R-wave and therefore incorrectly trigger recording of a magnetic resonance image. The situation can also occur where a "genuine" R-wave is not detected as such owing to the superimposed interference signals. This regularly leads to a significant deterioration in the image quality.

DE102009015385A1 describes a method for detecting R-waves which takes account of interferences of this kind.

A further problem that occurs independently of the imaging modality used is that of an examination object holding their breath in order to prevent or minimize movement artifacts in the imaging of a heart. Increased amplitudes of R-waves during a breath-holding phase make reliable R-wave detection difficult. Physiologically this effect may be explained in that in a deep breath-holding phase the heart tilts slightly due to a change in the volume of a lung and therefore the source of the underlying ECG signal is shifted. The derived ECG signal changes since the electrodes are still attached to the same place on the examination object, however. This effect occurs primarily during breath-holding in inspiration. Successful detection of R-waves is made difficult as a result.

DE102007059149A1 discloses a method for monitoring an examination person. In addition to image data, measurement data on cardiac activity and breathing activity is also recorded, with an operator being informed in the event of deviations following a comparison with a predetermined activity curve.

US2010/0174205A1 discloses the measurement of the variability of the heartbeat in which breathing commands are employed.

SUMMARY OF THE INVENTION

An object of the present invention is to provide a method that allows detection of R-waves, independently of a specific breathing position of an examination object.

This object is achieved in accordance with the invention by a method for determining R-waves in an ECG signal that includes the following steps.

At least one reference ECG signal are measured using an ECG measuring device.

At least one reference breathing signal is measured using a breathing device.

At least one reference R-wave is determined using the reference ECG signal and the reference breathing signal.

At least one reference value is determined using the reference ECG signal and the reference breathing signal.

At least one comparison rule is created based on the at least one reference value.

ECG signals and breathing signals are measured in which R-waves are to be determined.

The measured ECG signals and breathing signals are compared with the at least one reference value, using the at least one comparison rule.

At least one R-wave is determined using the measured ECG signals and breathing signals dependent on the result of the comparison.

Measuring at least one reference ECG signal using an ECG measuring device means that a reference ECG signal is measured on one channel at least of the ECG measuring device. The at least one reference ECG signal is recorded in an environment that is not disrupted by external influences.

Furthermore, at least one reference breathing signal is measured using a breathing device. This also preferably occurs in an environment that is not disrupted by external influences, for example outside of a medical imaging device.

The at least one reference R-wave is then determined using the reference ECG signal and the reference breathing signal. Two reference R-waves are advantageously determined and, more precisely, one during shallow breathing of an examination object and one during particularly deep breath-holding of the examination object. Different manifestations of R-waves during different breathing positions can therefore be detected.

The determination of at least one reference R-wave also includes detection of a value of the associated breathing signal.

The at least one reference value is then determined using the reference ECG signal and the reference breathing signal. Two reference values are advantageously determined and, more precisely, one during shallow breathing of an examination object and one during particularly deep breath-holding of the examination object. Different reference values can therefore be formed during different breathing positions, from which reference values further, current breathing signals may be derived.

The reference value can also be a curve of a value ascertained from the ECG signal over a period in a time interval. The value of the time interval can be largely freely predefined in this connection.

At least one comparison rule is then created on the basis of the at least one reference value. The comparison rule indicates as the result how subsequently measured ECG signals, in which an R-wave is to be determined, must correlate with the reference values if an R-wave exists.

The data that are to be analyzed are determined by the measurement of ECG signals and breathing signals in which R-waves are to be determined.

A comparison of the measured ECG signals and breathing signals with the at least one reference value is made using the at least one comparison rule, in order to be able to determine at least one R-wave using the measured ECG signals and breathing signals if the comparison is positive.

A measurement of a reference ECG signal and reference breathing signal, and the steps through to the creation of the comparison rule are advantageously carried out each time after the ECG measuring device has been applied to the examination object. A reference ECG signal and a reference breathing signal are implemented after the ECG measuring device has been applied to the examination object located on an examination couch of a medical imaging device until a process is started in the medical imaging device. Particularly current reference values can be determined in this way since an extensive stabilization of contact of the ECG measuring device with the examination object has occurred and there are still no disruptive influences of the medical imaging device on the ECG measuring device.

By determining a reference R-wave with the aid of a combination of reference ECG signal and reference breathing signal a reference value, and therefore a comparison rule, is ascertained which allows detection of R-waves, independently of a specific breathing position of an examination object.

In an advantageous embodiment the at least one reference ECG signal and the at least one reference breathing signal are measured by breathing commands. This also preferably occurs in an environment that is not disrupted by external influences, by way of example outside of a medical imaging device, with the breathing commands being applied analogously to use in the medical imaging device. A breathing command means a command given by an operator that provides specific instructions, such as "breathe in", "breathe out" and/or "hold your breath". A breathing pattern that is as detailed as possible is therefore reproduced during a learning process in order to optimize the results.

In a further embodiment at least two reference ECG signals and at least two reference breathing signals are measured which correspond to at least two different breathing commands respectively. The two different breathing commands preferably cover breathing situations of shallow breathing and breathing situations of preferably deep breath-holding. The breathing pattern inside the medical imaging device can therefore be reproduced and R-waves can be reliably detected.

In a preferred embodiment the at least one R-wave is determined using the measured ECG signals and breathing signals according to a breathing position. The current breathing position of the examination object should therefore be detected automatically and the R-wave determined according to the detected breathing position. This procedure allows the method to be used particularly flexibly.

In an embodiment, the comparison rule is created according to a pattern recognition method. A pattern recognition method means a method that automatically creates a comparison rule of this kind using learning data. Examples of methods of this kind are inter alia, but not exclusively, support vector machines, neural networks or hidden Markov models.

In a further embodiment, the breathing command is a signal that indicates successful determination of the at least one reference R-wave. A "signal" means, for example, an acoustic signal such as a sound which can indicate that the reference R-wave has been determined. A direct start can therefore be made with the actual examination.

In a preferred embodiment, the at least one reference breathing signal and/or the breathing signal are scaled. Inventive scaling also comprises purging of an offset. This is used to obtain a lower amplitude around a zero position primarily in the case of shallow breathing and therefore to increase the accuracy of the method.

In another embodiment, the determined at least one reference value comprises values which the reference ECG signal and the reference breathing signal assumes in a time interval, which begins before the at least one reference R-wave of the ECG signal and lasts until the occurrence of the at least one reference R-wave at most. A rising slope of a reference R-wave is primarily learnt in this way. This should reflect a characteristic increase and likewise increase the accuracy of the method.

The time interval therefore can be within the increase in the ECG signal between the points designated by "Q" and "R". If more than one ECG channel is detected the time interval advantageously begins as soon as the beginning of the increase between "Q" and "R" is detected in one of the channels, and ends as soon as the end of this increase is detected in the last of the channels. The time interval therefore has a duration in the order of about 12 to 20 milliseconds, of 50 to 60 milliseconds at most, before the R-wave. With such a choice of time interval further analysis of ECG signals within the time interval is due to the signal characteristic that is particularly distinctive there, for example due to a relatively high amplitude there, and a first derivative of the signal characteristic that is relatively high there.

In a further embodiment, the determined at least one reference value comprises values which the reference ECG signal and the reference breathing signal assumes in a time interval which begins before the at least one reference R-wave of the ECG signal and lasts over the occurrence of the at least one reference R-wave. Both a rising slope before a reference R-wave and a falling slope after a reference R-wave are learnt in this way. This should reflect a characteristic increase and decrease and likewise increase the accuracy of the method.

In a preferred embodiment, a trigger signal is emitted on the basis of at least one positive result of the comparison after the at least one R-wave has been determined using the measured ECG signals and breathing signals. In addition to the pure monitoring of a cardiac function of an examination object ECG signals can also be used in medical imaging to generate trigger signals. During imaging, information about a cardiac phase is obtained via the ECG signal in order to thereby synchronize the imaging with the cardiac activity. High quality heart scans or scans of regions which are moved by the heartbeat can be created in this way in particular in the case of imaging methods which require a relatively long recording time. Trigger signals are essential for this.

In another embodiment, at least one reference value is a signal value of a channel of the ECG measuring device at one instant at least in the time interval and/or its first and/or second time derivative(s).

In a further embodiment, at least one reference value is a value obtained from the signal values of at least two channels of ECG measuring device at one instant at least in the time interval, and/or its first and/or second time derivative(s).

An advantage of using the respective first and optionally second time derivative(s) of the described values is that these are not subjected to any offset variations.

In further preferred embodiments
- the at least one comparison rule comprises a determination of a deviation of the reference value from a corresponding value of the measured ECG signal as the result,
- the deviation occurs by way of the determination of an error, in particular the total of the error squares,
- the reference value is determined in each case in its course over the entire time interval,
- the comparison rule comprises the use of a matched filter and the outputting of a similarity value as the result,
- at least one reference value is the combined magnitude of the at least two channels,
- at least one reference value is a reference angle determined from the signal values of two channels respectively,
- the at least one comparison rule comprises a determination of a deviation of the reference value from a corresponding value of the measured ECG signal as the result and the emission of a trigger signal, which is emitted after the determination of the at least one R-wave using the measured ECG signals and breathing signals on the basis of at least one positive result of the comparison, occurs if the result of this comparison shows that the corresponding value of the measured ECG signal deviates from the reference angle by a predefinable angular range at most,
- the emission of a trigger signal, which is emitted after the determination of the at least one R-wave using the measured ECG signals and breathing signals on the basis of at least one positive result of the comparison, occurs if the determined deviation lies below a predefinable threshold value,
- the emission of a trigger signal, which is emitted after the determination of the at least one R-wave using the measured ECG signals and breathing signals on the basis of at least one positive result of the comparison, occurs if the result of the matched filter deviates from an ideal value of the similarity value of the matched filter by a predefinable value at most,
- at least one comparison rule is applied to a plurality of reference values and their corresponding values of the measured ECG signal to increase the robustness of the method,
- all results of the comparison must be positive for the emission of a trigger signal in order to likewise increase the robustness of the method,
- a smoothing filter, by way of example a low-pass filter which frees the ECG signals for example from high-frequency interference, is applied to ECG signals for determining reference values before the determination of the at least one reference value, and to measured ECG signals before the comparison
- the ECG measuring device comprises two channels, whose signal values or whose first or second time derivatives are determined as the reference value, wherein the two signal values or their first or second time derivatives are presented as a complex value whose real part is the signal value or its first or second time derivative of the first channel, and whose imaginary part is the signal value or its first or second time derivative of the second channel, and/or wherein the signal values of a plurality of channels are presented as a vector,
- a trigger signal is emitted only if, after receiving the at least one positive result, an extreme condition is also met in the measured ECG signal within a predefinable maximum duration,
- at least one reference value is a signal value of a channel of the ECG measuring device at one instant at least in the time interval, and/or its first and/or second time derivative(s), which reference value is used to create a comparison rule for determining a deviation of the reference value from a corresponding value of the measured ECG signal on the basis of the determination of an error, in particular the total of the error squares, and/or on the basis of a matched filter;

and/or wherein at least one reference value is a value obtained from the signal values of at least two channels of the ECG measuring device at one instant at least in the time interval, in particular a combined magnitude, and/or its first and/or second time derivative(s), which reference value is used to create a comparison rule for determining a deviation of the reference value from a corresponding value of the measured ECG signal on the basis of the determination of an error, in particular the total of the error squares, and/or on the basis of a matched filter;

and/or wherein at least one reference value is a reference angle determined from the signal values of two channels, which reference value is used to create a comparison rule for determining a deviation of the reference value from a corresponding value of the measured ECG signal.

Exemplary reference values, which can be obtained from the reference ECG signals, are:
- the signal values of the reference ECG signals in the time interval or in parts thereof,
- the first and optionally second time derivative of the signal values,
- a combined magnitude in the time interval or in parts thereof,
- the first and optionally second time derivative(s) of the combined magnitude and/or
- an ascertained reference angle RHO_ref at the instant of the occurrence of an R-wave in the reference ECG signal.

Consequently the following are therefore alternatively or respectively constantly ascertained from the measured ECG signals for comparison with the corresponding reference values:
  the signal values of the measured ECG signals,
  the first and optionally second time derivative(s) of the signal values,
  a combined magnitude of the measured ECG signals,
  the first and optionally second time derivative of the combined magnitude and/or
  an angle RHO in the measured ECG signal ascertained analogously to the reference angle RHO_ref.

The combined magnitude is formed by way of example by forming the root, the total of the values squared of the ECG signals, designated by way of example by S1 and S2: Mag= $\sqrt{S1^2+S2^2}$. This can occur particularly easily if the individual ECG signals in the time interval of individual channels are advantageously described as components of a vector V=(S1,S2), or in the case of exactly two channels as a complex number Z, where Re{Z}=S1 and Im{Z}=S2. Of course complex-valued vectors are also possible. The combined magnitude described above can therefore also be designated as the absolute value of the vector V or the complex number Z. In this case as well it is optionally not the entire course of the ECG signal in the time interval for calculation of the combined magnitude that is stored as the reference value. Instead, potentially only parts thereof are stored, for example individual measuring points in the course over time. If more than two channels are measured, for example three or more, the combined magnitude can be formed analogously by forming the root, the total of the values squared of the, for example, three or more ECG signals (S1, S2, S3, . . . ) of each measured channel: Mag= $\sqrt{(S1^2+S2^2+S3^2+...)}$.

Examples of combined magnitude are values which the individual values of the ECG signals used for the calculation thereof equivalently incorporate, and therefore reproduce the information of the ECG signals in a combined value. The consideration of a combined magnitude means that during a comparison of comparative values of measured ECG signals, which is described below, with the reference values, variations, for example in an individual measured channel or a few measured channels, can be advantageously compensated. This kind of determination of an R-wave by taking into consideration at least two ECG channels is therefore particularly robust.

A reference angle means an angle between the values of the ECG signals S1 and S2 at the instant of the occurrence of the R-wave that has already been determined, and this can be determined by way of example as follows:

$$RHO\_ref = \arctan\left(\frac{S1(t = Rwave)}{S2(t = Rwave)}\right).$$

A reference angle determined in this way therefore provides information about a phase delay that exists between the two channels due to the respective contact of the channels with the patient. If the individual ECG signals are combined in a vector V or a complex number Z the phase delay can be visualized as angle information in the ECG signals presented as trajectories. The phase delay between two channels during an ECG measurement generally remains constant during the course of physiological variations. Therefore, if an R-wave exists, even an angle between measured ECG signals, determined after determination of the reference angle, must not deviate significantly from the reference angle if a variation in the phases of the channels occurs that is not due to external influences, such as breathing movements. Angle information of this kind can therefore advantageously be used to further safeguard an R-wave detected in the ECG signal measured after determination of the reference values.

The comparative values described above are compared with the reference values using at least one comparison rule. Comparison criteria are, for example:
  determinations of errors, in particular by way of the total of the error squares and/or
  matched filters.

The total of the error squares is determined by way of example by the following formula:

$$SumQ(\tau) = \alpha_s \cdot \sum_{t=0}^{\Delta t} (|X(\tau - \Delta t + t) - LX(t)|)^2,$$

where LX(t) is the reference value, X(t) the measured corresponding comparative value, □t the time interval and □s a normalization factor which ensures that is zero if X(t) is identical to the reference value LX(τ) determined previously. An advantageous choice of the normalization factor is the reciprocal total of the reference values squared over the time interval. This value can also be called the "energy" of the reference value in the time interval.

A positive result of this comparison criterion is therefore a value equal to zero (ideal value), or a value which deviates from zero by a predefinable small threshold value at most.

A matched filter (MF) determines the similarity of a curve, here for example the course of the subsequently measured ECG signal or a value of the ECG signal corresponding to a reference value in the time interval as a comparative value, with a predefined curve, here a reference value, for example the course of the, for example first, time derivative of the combined magnitude of the reference ECG signals. Mathematically this advantageously occurs by forming the correlation of reference value and corresponding value, for example advantageously according to the following formula:

$$MF(\tau) = \alpha \cdot \sum_{t=0}^{\Delta t} X(\tau - \Delta t + t) \cdot LX^*(t),$$

where LX(t) is the reference value, X(t) the measured corresponding comparative value, which are each presented as complex-valued values, □t the time interval and □ a normalization factor which ensures that MF(τ) is equal to one if X(t) is identical to the reference value LX(τ) determined previously. The "*" means, as is conventional with complex numbers, that the conjugated-complex value is used. An advantageous choice of the normalization factor is again the reciprocal total of the reference values squared over the time interval. This value can also be called the "energy" of the reference value in the time interval.

A positive result of this comparison criterion is therefore a comparative value equal to one (ideal value), or a value which deviates downwards or upwards from one by a predefinable small threshold value at most. The upper or lower threshold can of course also be chosen so as to be equal in each case.

If the ECG signals are supplied to a smoothing filter, by way of example a low-pass filter, which frees the ECG signals for example from high-frequency interference and with which "filtered" reference values and comparative values obtained in this way the steps described above can, in particular additionally, be analogously carried out.

The results of the comparison described above with the unfiltered values, and the results of the filtered comparison ("and" operation; "AND") can be used as a condition for the emission of a trigger signal, or the results of the two comparisons can be used with an "or"-operation ("OR") as the condition for the emission of a trigger signal.

The duration of the method is lengthened overall by using a smoothing filter of this kind. The drawback of this longer duration, which is in the order of about 2 to 3 milliseconds, must be weighed up, as required, against the advantage of the interference-free signals for evaluation.

All results of the comparison rule must therefore be positive for particularly reliable determination of an R-wave in the measured ECG signals. At least one positive result can also be chosen to be sufficient, however, if the requirements for the accuracy of the determination of the R-wave do not have to satisfy any greater requirements for potential given reasons.

If a trigger signal is only emitted if, in addition, after finding a sufficient number of positive results of the criteria already described, the first time derivative of the combined magnitude, or at least one measured ECG signal value, deviates from zero only by a small, predefinable threshold value at most, then what is known as an extreme condition exists with which the existence of an extremum in the measured signal characteristic is determined, individually or combined over the channels. The instant of the existence of an R-wave can therefore be determined particularly accurately since an extremum of this kind, a maximum, exists there, and therefore a trigger signal can be emitted particularly accurately.

ECG signals are advantageously measured as a vector cardiogram VCG(t). The comparative values corresponding to the previously determined reference values $LVCG_{(f)}(t)$ can also be determined. An angle ρ(t), a time derivative of the signal $\vec{VCG}(t)$ and a time derivative of the combined magnitude $|\vec{VCG}(t)|$ can be ascertained from the measured ECG signals. As illustrated above, the ECG signal VCG(t) can firstly be filtered, by way of example by a low-pass filter. The values just mentioned can, on the one hand, likewise then be determined as the comparative values (ρ(t), $\vec{VCG}_f(t)$ and $|\vec{VCG}_f(t)|$) from the filtered ECG signal $VCG_f(t)$. The index "f" stands here for "filtered".

For the respectively ascertained comparative values $\vec{VCG}(t)$, $\vec{VCG}_f(t)$, $|\vec{VCG}(t)|$ and $|\vec{VCG}_f(t)|$, a comparison can again be made using the comparison criteria "total of the error squares" SumQ and a matched filter respectively, and using the ascertained angle ρ(t) a simple threshold value comparison, for example with an upper and a lower threshold $ρ_H$ and $ρ_L$, can be made with the aid of the reference values $LVCG_{(f)}(t)$ (the index "f" is in brackets here since a filtering was performed or not performed according to the associated comparative values in each case).

After filtering, the first time derivative of an ECG signal of a first channel $\vec{VCG1}_f(t)$, the second time derivative of the ECG signal of the first channel $\vec{VCG1}_f(t)$ and the first and second derivative of an ECG signal of a second channel $\vec{VCG2}_f(t)$, $\vec{VCG2}_f(t)$ can be determined. A comparison can again be made here with the aid of the corresponding reference values $LVCG_{(f)}(t)$ for the ascertained comparative values $\vec{VCG1}_f(t)$, $\vec{VCG1}_f(t)$, $\vec{VCG2}_f(t)$ and $\vec{VCG2}_f(t)$ with the comparison criteria "total of the error squares" SumQ and a matched filter. An advantageous detection of R-waves is therefore achieved on the basis of ECG signals of individual channels in each case. This is advantageous in particular in cases in which in one or a few of the channel(s) of the ECG measuring device an ECG signal measured during the desired detection of R-waves does not already match the reference R-wave learnt by the reference values in the other channels, however. This can occur for example if a patient has to alternately breathe deeply and hold his breath during the measurement, whereby the position of his heart can change. In a case such as this, the detection of the R-wave by way of the comparison criteria described above, which work with comparative values and reference values which each process the ECG signals of a plurality of channels in a shared value, is no longer reliably possible. Particularly reliable detection of R-waves can be ensured by checking the ECG signals of the individual channels as well, advantageously in addition to checking said shared values. The additional checking of the second derivative in addition to the first derivative of the ECG signals of individual channels in a comparison that has been made in turn increases the amount of data, and therewith the reliability of the determination of the R-waves.

If the result is positive ("AND") for each of the comparisons described above, the first time derivative of the combined magnitude may also be considered for the filtered and the unfiltered values or the first time derivative of the ECG signals of the first and second channels.

To then ensure detection of R-waves independently of a specific breathing position of an examination object as well, the associated values of a breathing signal are also taken into account, as described above, in addition to the vector entries which characterize the ECG in the case of shallow breathing and breath-holding.

Due to the wide choice of comparison criteria a procedure of this kind of choosing and linking reference values and comparative values provides particularly good safeguarding of the whole method for determining an R-wave.

An ECG measuring device and a medical imaging device for determining R-waves in an ECG signal are also provided within the scope of the present invention.

The ECG measuring device and the medical imaging device includes a processor, an arithmetic unit, a memory unit and a breathing device that are configured to measure at least one reference ECG signal by operation of the processor, measure at least one reference breathing signal using the breathing device, determine at least one reference R-wave using the reference ECG signal and the reference breathing signal, determine at least one reference value using the reference ECG signal and the reference breathing signal by operation of the processor, create at least one comparison rule on the basis of the at least one reference value by operation of the arithmetic unit, measure ECG signals and breathing signals in which R-waves are to be determined by operation of the processor and/or the breathing device, compare the measured ECG signals and breathing signals with the at least one reference value using the at least one comparison rule by operation of the arithmetic unit, and determine at least one R-wave using the measured ECG signals and breathing signals by operation of the processor.

The present invention also encompasses a storage medium that can be loaded in a memory unit of a programmable controller or an arithmetic unit of a medical imaging apparatus and/or an ECG measuring device. The storage medium is encoded with programming instructions that cause the controller to execute any or all embodiments of the inventive method or different embodiments that have been described above. The programming instructions may require program resources, for example libraries and help functions, to implement the corresponding embodiments of the method.

The electronically readable storage medium may be, for example a DVD, magnetic tape or USB stick, on which electronically readable control information, in particular software, is stored.

The advantages of the inventive medical imaging device, the ECG measuring device, and the inventive electronically readable storage medium substantially correspond to the advantages of the inventive method that have been described above in detail. Features, advantages or alternative embodiments mentioned in this connection are likewise applicable to the other aspects of the invention. The corresponding functional features of the method are formed by appropriate representational modules, in particular by hardware modules.

DESCRIPTION OF THE PREFERRED EMBODIMENTS

Figure 1:
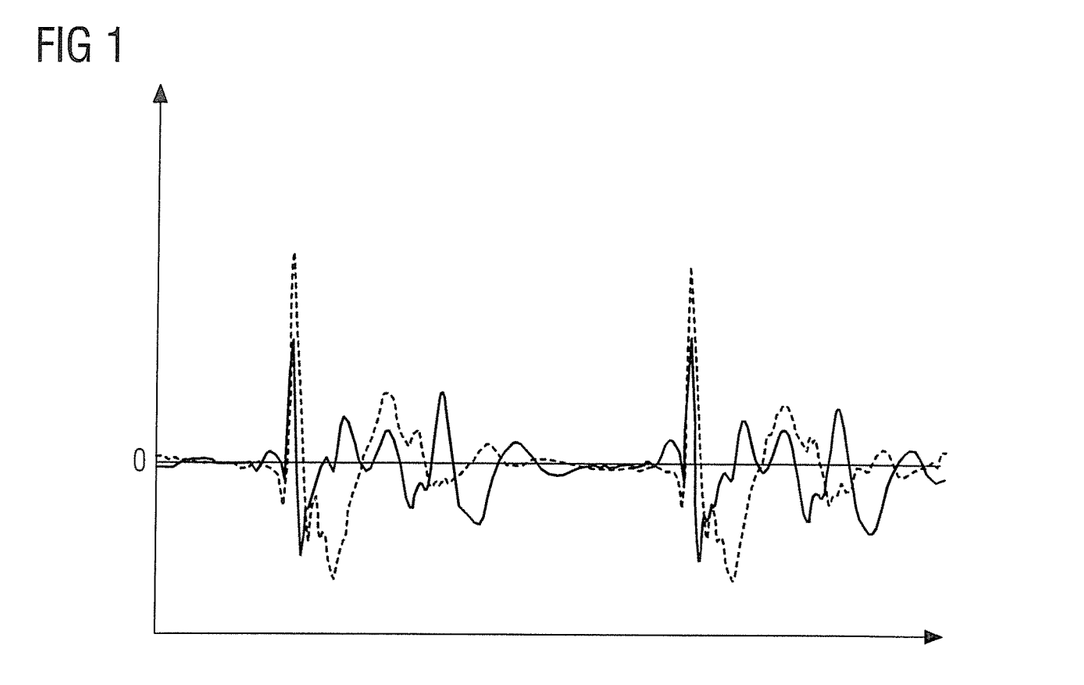
FIG. 1 shows a curve of an ECG signal over time in the case of shallow breathing of an examination object.

FIG. 1 shows a curve of an ECG signal having two channels over time in the case of shallow breathing of an examination object. The ECG signal is shown as the voltage U over time. Characteristic curves of the ECG signal are identified according to Einthoven by the letters P, Q, R, S and T and conventionally reproduce the various phases of a heartbeat.

Figure 2:
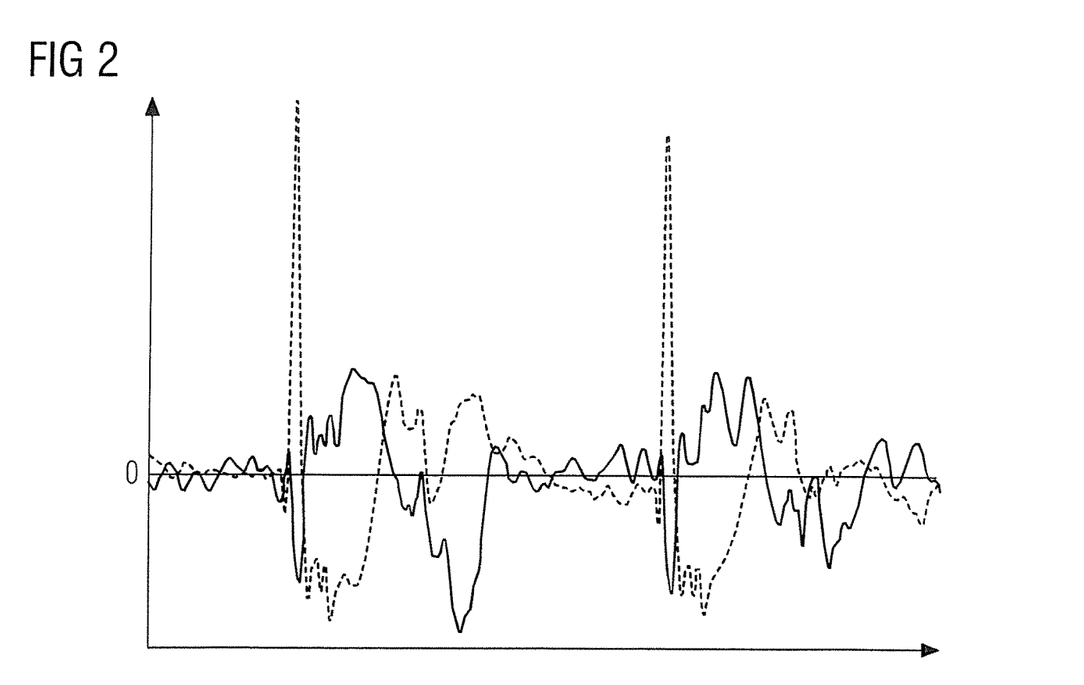
FIG. 2 shows a curve of an ECG signal over time in the case of breath-holding of an examination object.

FIG. 2 shows a curve of an ECG signal having two channels over time in the case of breath-holding of an examination object. The ECG signal is shown as the voltage U over time.

It can be seen that the curve of the ECG signal in FIG. 2 differs markedly from that in FIG. 1. The amplitude of the R-wave of ECG channel CH1 is increased in FIG. 2 by about 50% compared to the amplitude of the R-wave of ECG channel CH1 in FIG. 1. By contrast, the R-wave of ECG channel CH2 in FIG. 2 can barely still be seen, although the R-wave of ECG channel CH2 in FIG. 1 can be seen very clearly.

Physiologically this effect may be explained in that in a deep breath-holding phase the heart tilts slightly in the chest due to a change in the volume of the lungs. The source of the underlying ECG signal is shifted thereby. The derived ECG signal changes since the electrodes are still attached to the same location of the examination object, however. This effect primarily occurs in the case of breath-holding in inspiration. Successful detection of R-waves is made more difficult thereby.

Figure 3:
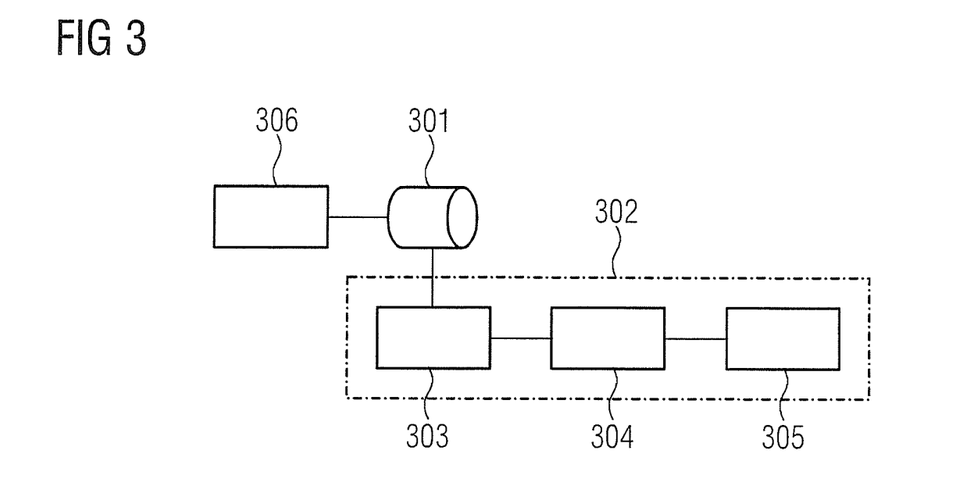
FIG. 3 shows an inventive medical imaging apparatus.

FIG. 3 shows an inventive medical imaging apparatus 301. The medical imaging device 301 has an ECG measuring device 302, a processor 303, an arithmetic unit 304 and a memory unit 305 and is designed for determining R-waves in an ECG signal.

The medical imaging apparatus 301 also has a breathing device 306 for measuring at least one reference breathing signal and for measuring breathing signals with the aid of which R-waves are to be determined.

The breathing device 306 can be designed as an independent unit but it may also be incorporated in the ECG measuring device 302.

The medical imaging device 301 is designed here as a pure magnetic resonance device. Alternatively the medical imaging apparatus 301 may also include a combined magnetic resonance positron emission tomography device, a computer tomography device or another imaging device known to a person skilled in the art.

Figure 4:
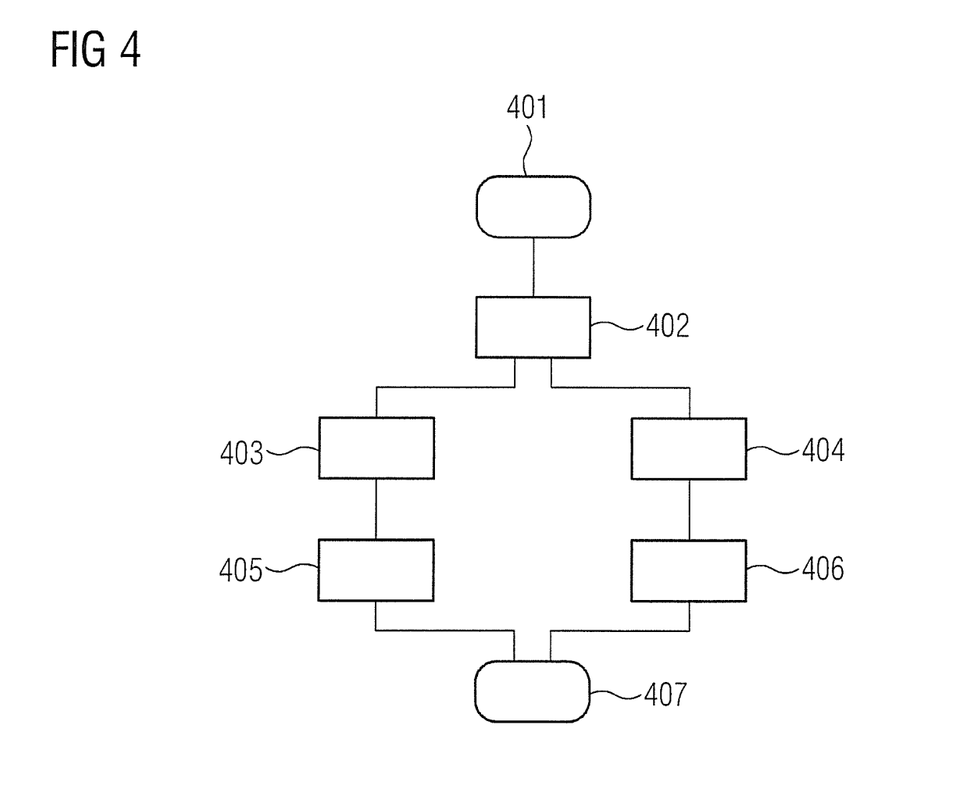
FIG. 4 is a flowchart for obtaining inventive signal vectors.

FIG. 4 is a flowchart for obtaining inventive signal vectors which can be used as the reference values.

The method includes the method steps 401 to 407, wherein parts of the description, including the corresponding reference numerals introduced in connection with the other figures, are also used in the description of the method steps 401 to 407.

Method step 401 is the start of a method for obtaining inventive signal vectors.

As described above, ECG signals are measured during a method step 402 as a vector cardiogram VCG(t). Since in principle a distinction should be made between breathing phases of shallow breathing and breathing phases where the breath is held, vectors are formed which characterize the two breathing phases. The following examples describe two-channel ECG vectors, but are not limited to these.

In method step 403, CH1_f[n] and CH2_f[n] with n chosen from $\{1, 2, \ldots, N\}$ describe an ECG signal in the case of shallow breathing. In method step 404 CH1_h1[n] and CH2_h1[n] with n chosen from $\{1, 2, \ldots, N\}$ describe an ECG signal where the breath is held in particular after deep inspiration. a[k] describes a breathing signal of a breathing device 306. The breathing signal is preferably scaled in such a way and/or purged of an offset in such a way that it only has a low amplitude around a zero position in the case of shallow breathing of an examination object.

CH1[n, a[k]] and CH2[n, a[k]], the two ECG channel signals that are to be learned and/or determined, are calculated as follows during method steps 405 and 406:

$$CH1[n,a[k]]=CH1\_f[n]+(CH1\_h1[n]-CH1\_f[n])*a[k]/a\_h1,$$

$$CH2[n,a[k]]=CH2\_f[n]+(CH2\_h1[n]-CH2\_f[n])*a[k]/a\_h1.$$

ECG signals in two ECG channels CH1[k] and CH2[k] are therefore trained during shallow breathing and during a phase of breath-holding and the associated value of the breathing signal a_h1 is noted. In this way a switch can then be smoothly made as a function of a current breathing signal a[k] between the extreme cases of shallow breathing and deep breath-holding, so advantageously there is always a reference value available that describes an optimally appropriate reference R-wave for the R-waves detection, irrespective of breathing or breath-holding.

Method step 407 marks the end of a method for obtaining inventive signal vectors.

In an alternative embodiment CH1_f[n] and CH2_f[n] are also trained in phases of breath-holding. The corresponding vectors are then CH1_h0[n] and CH2_h0[n] and the value of the breathing signal a_h0.

CH1[n, a[k]] and CH2[n, a[k]], the two ECG channel signals to be learned and/or determined are then calculated as follows:

$$CH1[n,a[k]]=CH1\_h0[n]+(CH1\_h1[n]-CH1\_h0[n])*\\(a[k]-a\_h0)/(a\_h1-a\_h0),$$

$$CH2[n,a[k]]=CH2\_h0[n]+(CH2\_h1[n]-CH2\_h0[n])*\\(a[k]-a\_h0)/(a\_h1-a\_h0).$$

In a further alternative embodiment more than two supporting points for the equations just described may also be used.

Reference values, which are eminently suitable as the basis for comparison and take account of the breathing, are therefore given in both specific exemplary embodiments illustrated here in the form of the signal vectors, while also taking into account the reference breathing signals during recording of the reference ECG signals for all current breathing phases or breathing signals a[k].

The comparison rule can preferably be derived herefrom according to a pattern recognition algorithm. The time interval covered by the instants [n] can refer to the rising slope of the reference R-waves or to the rising and falling slope of the reference R-waves combined.

Figure 5:
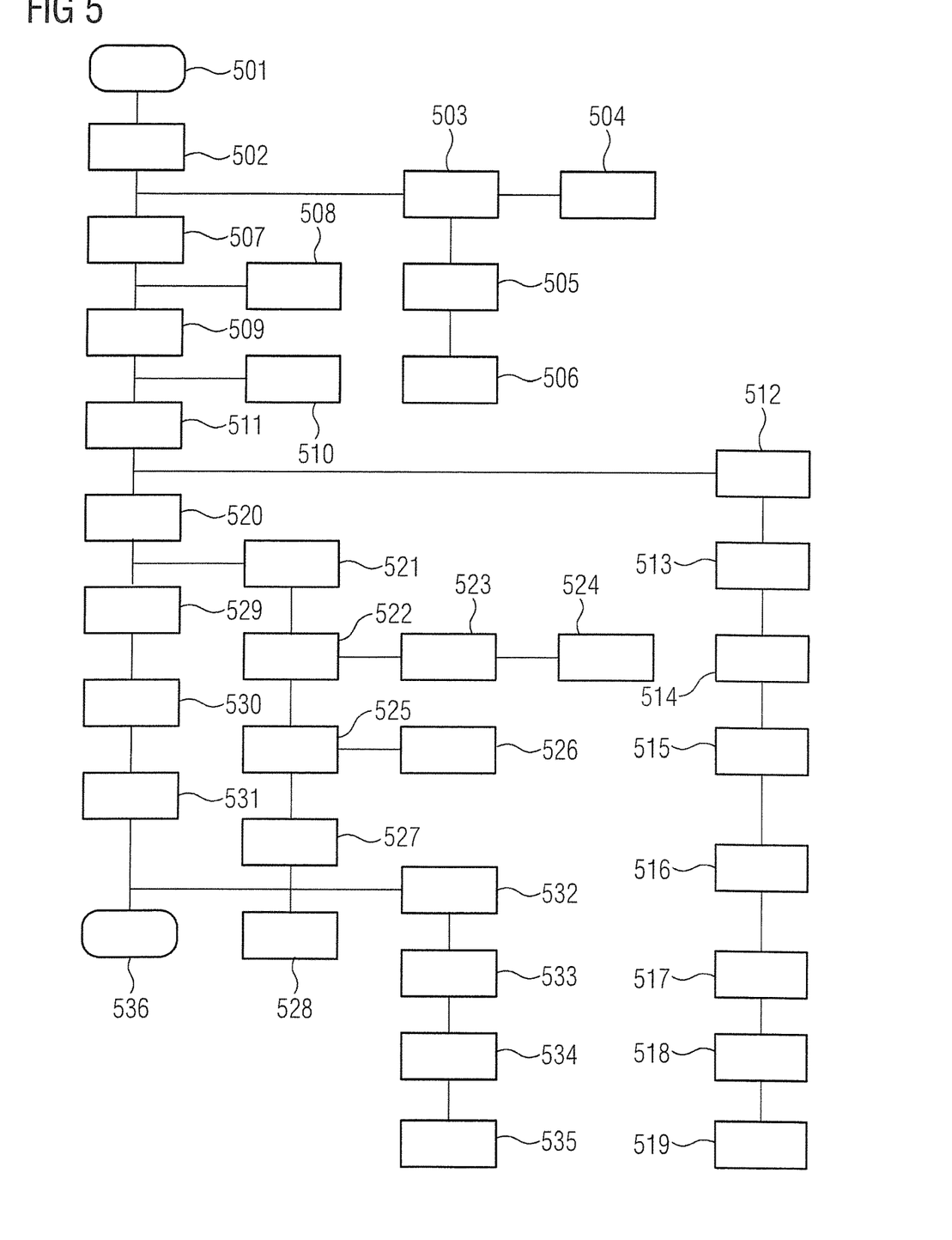
FIG. 5 is a flowchart of the inventive method.

FIG. 5 is a flowchart of an inventive method.

The method comprises method steps 501 to 536, wherein parts of the description, including the corresponding reference numerals introduced in connection with the other figures, are also used in the description of the method steps 501 to 536.

Method step 501 is the start of a method for determining R-waves in an ECG signal.

At least one reference ECG signal is measured using an ECG measuring device 302 during a method step 502. A measurement of at least one reference ECG signal using an ECG measuring device 302 is taken to mean a reference ECG signal which is measured on one channel at least of the ECG measuring device. The at least one reference ECG signal is incorporated in an environment that is not disrupted by external influences.

Method step 503 is the measurement of the at least one reference ECG signal and of the at least one reference breathing signal by means of a breathing command. This also preferably occurs in an environment that is not disrupted by external influences, for example outside of a medical imaging device, with the breathing commands being applied analogously to the use in a medical imaging device, however. A breathing command is taken to mean a command from an operator which comprises specific commands such as "breathe in", "breathe out" and/or "hold your breath". A breathing pattern that is as detailed as possible is therefore reproduced during a learning process in order to optimize the results.

During method step 504, the breathing command comprises a signal which indicates a successful determination of the at least one reference R-wave. A signal can be taken to mean by way of example an acoustic signal, such as a sound, which can indicate that the reference R-wave has been determined.

In method step 505, at least two reference ECG signals and at least two reference breathing signals are measured which correspond to at least two different breathing commands in each case. The two different breathing commands preferably comprise breathing situations of shallow breathing and breathing situations involving breath-holding. The breathing pattern inside the medical imaging device can therefore be reproduced and R-waves can be reliably detected.

In method step 506, the ECG measuring device 302 comprises two channels whose signal values or whose first or second time derivatives are determined as the reference value, with the two signal values or their first or second time derivatives being presented as a complex value whose real part is the signal value or its first or second time derivative of the first channel, and whose imaginary part is the signal value or its first or second time derivative of the second channel, and/or with the signal values of a plurality of channels being presented as a vector.

At least one reference breathing signal is measured using a breathing device during a method step 507. This also preferably occurs in an environment that is not disrupted by external influences, for example outside of a medical imaging device.

In method step 508, the at least one reference breathing signal and/or the breathing signal are scaled. Inventive scaling also comprises purging of an offset. This is used to obtain a low amplitude around a zero position primarily in the case of shallow breathing and therefore to obtain an increase in the accuracy of the method.

At least one reference R-wave is determined during a method step 509 using the reference ECG signal and the reference breathing signal. Two reference R-waves are advantageously determined and, more precisely, one in the case of shallow breathing of an examination object and one during breath-holding of the examination object. Different manifestations of R-waves during different breathing positions can therefore be detected. The determination of at least one reference R-wave can advantageously also include detection of a value of the associated breathing signal in a combined step.

In method step 510, a smoothing filter is applied to ECG signals for determining reference values before the determination of the at least one reference value, and to measured ECG signals before the comparison.

Method step 511 is a determination of at least one reference value using the reference ECG signal and the reference breathing signal. Two reference R-waves are advantageously determined and, more precisely, one in the case of shallow breathing of an examination object and one during breath-holding of the examination object. Different reference values can therefore be formed during different breathing positions. The reference value can also be a characteristic of a value obtained from the ECG signal ascertained over a period in a time interval. The size of the time interval can be largely freely specified in this connection.

Exemplary reference values, which can be determined from the reference ECG signals, are:
- the signal values of the reference ECG signals in the time interval or in parts thereof,
- the first and optionally second time derivative of the signal values,
- a combined magnitude in the time interval or in parts thereof,
- the first and optionally second time derivative of the combined magnitude and/or
- an ascertained reference angle RHO_ref at the instant of the occurrence of an R-wave in the reference ECG signal.

Consequently the following are therefore alternatively or respectively constantly ascertained from the measured ECG signals for comparison with the corresponding reference values:

the signal values of the measured ECG signals,
the first and optionally second time derivative(s) of the signal values,
a combined magnitude of the measured ECG signals,
the first and optionally second time derivative(s) of the combined magnitude and/or
an angle RHO in the measured ECG signal ascertained analogously to the reference angle RHO_ref.

In method step 512, the determined at least one reference value comprises values which the reference ECG signal and the reference breathing signal assumes in a time interval which begins before the at least one reference R-wave of the ECG signal and lasts at most until the occurrence of the at least one reference R-wave. A rising slope of a reference R-wave is primarily learnt in this way. The time interval, for example within the increase in the ECG signal, therefore lies between the points denoted by "Q" and "R". If more than one ECG channel is detected, the time interval advantageously begins as soon as the beginning of the increase between "Q" and "R" is detected in one of the channels, and ends as soon as the end of this increase is detected in the last of the channels. The time interval therefore has a duration in the order of about 12 to 20 milliseconds, 50 to 60 milliseconds at most, before the R-wave. With such a choice of the time interval, further analysis of ECG signals within the time interval is due to the signal characteristic that is particularly distinctive there, for example due to a relatively high amplitude there, and a first derivative of the signal characteristic that is relatively high there.

In method step 513, the determined at least one reference value comprises values which the reference ECG signal and the reference breathing signal assumes in a time interval which begins before the at least one reference R-wave of the ECG signal and lasts over the occurrence of the at least one reference R-wave. A rising slope before a reference R-wave and a falling slope after a reference R-wave are learnt in this way.

In method step 514, at least one reference value is a signal value of a channel of the ECG measuring device 302 at one instant at least in the time interval and/or its first and/or second time derivative(s).

In method step 515, at least one reference value is a value obtained from the signal values of at least two channels of the ECG measuring device 302 at one instant at least in the time interval, and/or its first and/or second time derivative(s).

Method step 516 is a determination of the reference value in its course over the entire time interval in each case.

In method step 517, at least one reference value is the combined magnitude of the at least two channels.

In method step 518, at least one reference value is a reference angle determined from the signal values of two channels respectively.

In method step 519, at least one reference value is a signal value of a channel of the ECG measuring device 302 at one instant at least in the time interval, and/or its first and/or second time derivative(s), which reference value is used to create a comparison rule for determining a deviation of the reference value from a corresponding value of the measured ECG signal on the basis of the determination of an error, in particular the total of the error squares, and/or on the basis of a matched filter;

and/or at least one reference value is a value obtained from the signal values of at least two channels of the ECG measuring device (302) at one instant at least in the time interval, in particular a combined magnitude, and/or its first and/or second time derivative, which reference value is used to create a comparison rule for determining a deviation of the reference value from a corresponding value of the measured ECG signal on the basis of the determination of an error, in particular the total of the error squares, and/or on the basis of a matched filter;

and/or at least one reference value is a reference angle determined from the signal values of two channels, which reference value is used to create a comparison rule for determining a deviation of the reference value from a corresponding value of the measured ECG signal.

During a method step 520, at least one comparison rule is created on the basis of the at least one reference value. As the result the comparison rule indicates how subsequently measured ECG signals, in which an R-wave is to be determined, must correlate with the reference values if an R-wave exists.

Method step 521 includes the creation of the comparison rule according to a pattern recognition method. A pattern recognition method is taken to mean a method that automatically creates a comparison rule of this kind using learning data. Examples of methods of this kind are inter alia, but not exclusively, support vector machines, neural networks or hidden Markov models.

In method step 522, the at least one comparison rule comprises a determination of a deviation of the reference value from a corresponding value of the measured ECG signal as the result.

In method step 523, the deviation occurs by way of the determination of an error, in particular the total of the error squares.

Method step 524 marks the emission of a trigger signal, which is emitted after the determination of the at least one R-wave using the measured ECG signals and breathing signals on the basis of at least one positive result of the comparison, which then occurs if the determined deviation lies below a predefinable threshold value.

In method step 525, the comparison rule comprises the application of a matched filter and the outputting of a similarity value as the result.

During method step 526, a trigger signal is emitted, which is emitted after the determination of the at least one R-wave using the measured ECG signals and breathing signals on the basis of at least one positive result of the comparison and, more precisely, if the result of the matched filter deviates from an ideal value of the similarity value of the matched filter by a predefinable value at most.

In method step 527, the at least one comparison rule includes a determination of a deviation of the reference value from a corresponding value of the measured ECG signal as the result and the emission of a trigger signal, which is emitted after the determination of the at least one R-wave using the measured ECG signals and breathing signals on the basis of at least one positive result of the comparison if the result of this comparison shows that the corresponding value of the measured ECG signal deviates from the reference angle by a predefinable angular range at most.

In method step 528, the at least one comparison rule is applied to a plurality of reference values and their corresponding values of the measured ECG signal.

Method step 529 is the measurement of ECG signals and breathing signals in which R-waves are to be determined. The data to be analyzed is determined thereby.

In method step 530, comparisons of the measured ECG signals and breathing signals are made with the at least one reference value using the at least one comparison rule in order to be able to determine at least one R-wave using the measured ECG signals and breathing signals.

Comparison criteria are, for example:
error determinations, in particular by way of the total of the error squares and/or
matched filters.

Method step 531 is the determination of at least one R-wave using the measured ECG signals and breathing signals. A reference value, and therefore a comparison rule, is consequently ascertained which allows detection of R-waves independently of a specific breathing position of an examination object.

In method step 532, the at least one R-wave is determined using the measured ECG signals and breathing signals according to a breathing position. The current breathing position of the examination object should therefore preferably be automatically determined in this way and the R-wave determined according to the detected breathing position.

In method step 533, a trigger signal is emitted on the basis of at least one positive result of the comparison after the determination of the at least one R-wave using the measured ECG signals and breathing signals. In addition to pure monitoring of a cardiac function of an examination object, ECG signals can also be used in medical imaging to generate trigger signals. Information about a cardiac phase is obtained by way of the ECG signal during imaging in order to thereby synchronize imaging with cardiac activity. High quality heart scans or scans of regions which are moved by the heartbeat can be created in this way in particular in the case of imaging methods which require a relatively long recording time. Trigger signals are essential for this.

In method step 534, all results of the comparison must be positive for a trigger signal to be emitted.

During method step 535, a trigger signal is only emitted if, after receiving the at least one positive result, an extreme condition is also met in the measured ECG signal within a predefinable maximum duration method.

Method step 536 is the end of a method for determining R-waves in an ECG signal.

In summary, the invention concerns a method for determining R-waves in an ECG signal, that includes the following steps:
measuring at least one reference ECG signal using an ECG measuring device,
measuring at least one reference breathing signal using a breathing device,
determining at least one reference R-wave using the reference ECG signal and the reference breathing signal,
determining at least one reference value using the reference ECG signal and the reference breathing signal,
creating at least one comparison rule on the basis of the at least one reference value,
measuring ECG signals and breathing signals in which R-waves are to be determined,
comparing the measured ECG signals and breathing signals with the at least one reference value using the at least one comparison rule, and
determining at least one R-wave using the measured ECG signals and breathing signals.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for determining R-waves in an ECG signal, comprising:
    measuring a first reference ECG signal and a second reference ECG signal;
    measuring a first reference breathing signal and a second reference breathing signal, the first reference breathing signal and the second reference breathing signal corresponding to different breathing types that occur during the measurement of the first reference ECG signal and the second reference ECG signal, respectively;
    in a processor, determining (i) a first reference R-wave using the first reference ECG signal and the first reference breathing signal, and (ii) a second reference R-wave using the second reference ECG signal and the second reference breathing signal;
    in said processor, determining (i) a first reference value using the first reference ECG signal and the first reference breathing signal, and (ii) a second reference value using the second reference ECG signal and the second reference breathing signal;
    in said processor, automatically creating at least one comparison rule on the basis of the first reference value and the second reference value, the at least one comparison rule indicating how subsequently measured ECG signals should correlate with each of the first reference value and the second reference value to detect the existence of an R-wave in the subsequently measured ECG signals based upon a respective breathing signal that is measured during each of the subsequently measured ECG signals;
    measuring, as the subsequently measured ECG signals, ECG signals in which R-waves are to be determined;
    measuring the breathing signals during the measuring of the subsequently measured ECG signals;
    in said processor, comparing the subsequently measured ECG signals and the measured breathing signals with the first reference value and the second reference value using the at least one comparison rule; and
    in said processor, detecting a presence of at least one R-wave in the subsequently measured ECG signals on the basis of at least one positive result of the comparison of the subsequently measured ECG signals and the measured breathing signals with the first reference value and the second reference value using the at least one comparison rule,
    wherein a breathing type that occurs during measurement of the first reference ECG signal corresponds to patient breathing, and
    wherein a breathing type that occurs during the measurement of the second reference ECG signal corresponds to patient breath-holding.

2. The method as claimed in claim 1, comprising measuring the first and the second reference ECG signal and the first and the second reference breathing signal by use of breathing commands.

3. The method as claimed in claim 2, comprising:
    generating an indicator signal that indicates a successful detection of the first or the second reference R-wave.

4. The method as claimed in claims 1, comprising scaling at least one of (i) the first and the second reference breathing signal, or (ii) the first and the second breathing signal.

5. The method as claimed in claim 1, comprising determining the at least one of the first or the second reference value using values of the first or the second reference ECG signal and the first or the second reference breathing signal, respectively, that occur in a time interval that begins before the first or the second reference R-wave of the ECG signal and lasts until the occurrence of the first or the second reference R-wave at most, respectively.

6. The method as claimed in claim 1, comprising determining at least one of the first or the second reference value using values of the first or the second reference ECG signal and the first or the second reference breathing signal that occur, respectively, in a time interval that begins before the first or the second reference R-wave of the ECG signal and lasts over the occurrence of the first or the second reference R-wave, respectively.

7. The method as claimed in claim 1, comprising, after the detection of the first or the second R-wave using the subsequently measured ECG signals and the measured breathing signals, respectively, emitting a trigger signal based on at least one positive result of the respective comparison.

8. The method as claimed in claim 7, comprising emitting the trigger signal if a determined deviation in the first and the second reference value from a corresponding respective value of the first and the second subsequently measured ECG signal lies below a predefinable threshold value.

9. The method as claimed in claim 1, comprising determining the first or the second reference value as a signal value of a respective ECG channel associated with a medical imaging apparatus at a time within a duration selected from the group consisting of a time interval, the first time derivative of said time interval, and the second time derivative of said time interval.

10. The method as claimed in claim 9, comprising determining the first or the second reference value, respectively in each case, over an entirety of the time interval.

11. The method as claimed in claim 10, comprising creating the at least one comparison rule using a matched filter and emitting a similarity value as the result.

12. The method as claimed in claim 11, comprising emitting a trigger signal after the detection of the first or the second R-wave using the subsequently measured ECG signals and the measured breathing signals on the basis of at least one positive result of the respective comparison, if the result of the matched filter deviates from an ideal value of the similarity value of the matched filter by a predefinable value.

13. The method as claimed in claim 1, comprising creating the at least one comparison rule based upon a deviation in the first and the second reference value from a corresponding respective value of the first and the second subsequently measured ECG signal.

14. The method as claimed in claim 13, wherein the deviation in the first and the second reference value is based upon a sum of squares error.

15. The method as claimed in claim 1, comprising, after the detection of the first or the second R-wave using the subsequently measured ECG signals and the measured breathing signals, emitting a trigger signal based on at least one positive result of the comparison,
wherein results of the comparison are positive for a trigger signal to be emitted.

16. The method as claimed in claim 15, comprising:
applying a smoothing filter to the subsequently measured ECG signals before the act of comparing the subsequently measured ECG signals and the measured breathing signals with the first and the second reference value.

17. The method as claimed in claim 1, wherein the subsequently measured ECG signals comprise two channels having signal values or first or second time derivatives that are determined as the first or the second reference value, respectively,
wherein the signal values or the first or second time derivative thereof are represented as a complex value having a real part that is the signal value or a first or a second time derivative of the first channel, and having an imaginary part that is the signal value or a first or a second time derivative of the second channel, and/or
wherein the signal values of a plurality of channels are represented as a vector.

18. The method as claimed in claim 1, comprising, after the detection of the first or the second R-wave using the subsequently measured ECG signals and the measured breathing signals, emitting a trigger signal based on at least one positive result of the comparison, and emitting a trigger signal only if, after receiving the at least one positive result, a condition is met within a predefinable maximum duration in the measured ECG signal.

19. The method as claimed in claim 1, wherein the first or the second reference value is a signal value of a signal channel at one instant at least in a time interval, and/or a first and/or a second time derivative(s), which corresponding reference value is used to create the at least one comparison rule for determining a deviation in the first or the second reference value from a corresponding respective value of the measured ECG signal on the basis of the determination of a total of the error squares, and/or on the basis of a matched filter.

20. The method as claimed in claim 1, comprising creating the at least one comparison rule according to a pattern recognition method.

21. The method as claimed in claim 1, wherein the first reference ECG signal and the first reference breathing signal used to determine the first reference R-wave correspond to a phase of the breathing, and
wherein the second reference ECG signal and the second reference breathing signal used to determine the second reference R-wave correspond to a phase of the breath-holding.

22. An imaging apparatus comprising:
a medical imaging scanner; and
a processor configured to determine (i) a first reference R-wave using a first measured reference ECG signal and a first measured reference breathing signal, and (ii) a second reference R-wave using a second measured reference ECG signal and a second measured reference breathing signal, the first measured reference breathing signal and the second measured reference breathing signal corresponding to different breathing types that occur during the measurement of the first measured reference ECG signal and the second measured reference ECG signal, respectively;
said processor being configured to determine (i) a first reference value using the first measured reference ECG signal and the first measured reference breathing signal, and (ii) a second reference value using the second measured reference ECG signal and the second measured reference breathing signal;
said processor being configured to automatically create at least one comparison rule on the basis of the first reference value and the second reference value, the at least one comparison rule indicating how subsequently measured ECG signals should correlate with each of the first reference value and the second reference value to detect the existence of an R-wave in the subsequently measured ECG signals based upon a respective breathing signal that is measured during each of the subsequently measured ECG signals;

said processor being configured to compare the subsequently measured ECG signals and the measured breathing signals with the first reference value and the second reference value using the at least one comparison rule, the measured breathing signals being used to determine R-waves in the subsequently measured ECG signals; and said processor being configured to detect a presence of at least one R-wave in the subsequently measured ECG signals on the basis of at least one positive result of the comparison of the subsequently measured ECG signals and the measured breathing signals with the first reference value or the second reference value using the at least one comparison rule, wherein a breathing type that occurs during the measurement of the first measured reference ECG signal corresponds to patient breathing, and wherein a breathing type that occurs during the measurement of the second measured reference ECG signal corresponds to patient breath-holding.

23. An ECG measuring device as claimed in claim 22, wherein the processor comprises a smoothing filter that smooths said subsequently measured ECG signals.

24. A non-transitory, computer-readable data storage medium encoded with programming instructions, and storage medium being loaded into a control computer of a medical imaging apparatus, which also comprises a medical imaging scanner, said programming instructions causing said control computer to:

receive a first measured reference ECG signal and a second measured reference ECG signal;

receive a measured first reference breathing signal and a second measured reference breathing signal, the first measured reference breathing signal and the second measured reference breathing signal corresponding to different breathing types that occur during the measurement of the first measured reference ECG signal and the second measured reference ECG signal, respectively;

determine (i) a first reference R-wave using the first measured reference ECG signal and the first measured reference breathing signal, and (ii) a second reference R-wave using the second measured reference ECG signal and the second measured reference breathing signal;

determine (i) a first reference value using the first measured reference ECG signal and the first measured reference breathing signal, and (ii) a second reference value using the second measured reference ECG signal and the second measured reference breathing signal;

automatically generate at least one comparison rule on the basis of the first reference value and the second reference value, the comparison rule indicating how subsequently measured ECG signals should correlate with the each of the first reference value and the second reference value to detect the existence of an R-wave in the subsequently measured ECG signals based upon a respective breathing signal that is measured during each of the subsequently measured ECG signals;

compare the subsequently measured ECG signals and the measured breathing signals with the first reference value and the second reference value using the at least one comparison rule, the subsequently measured breathing signals being used to determine R-waves in the subsequently measured ECG signals; and detect a presence of at least one R-wave in the subsequently measured ECG signals on the basis of at least one positive result of the comparison of the subsequently measured ECG signals and the measured breathing signals with the first reference value and the second reference value using the at least one comparison rule, wherein a breathing type that occurs during the measurement of the first measured reference ECG signal corresponds to patient breathing, and wherein a breathing type that occurs during the measurement of the second measured reference ECG signal corresponds to patient breath-holding.

* * * * *